United States Patent [19]

Magerlein

[11] 4,031,081
[45] June 21, 1977

[54] BICYCLIC INTERMEDIATES FOR PREPARING 16-FLUORINATED PROSTAGLANDIN ANALOGS

[75] Inventor: Barney J. Magerlein, Portage, Mich.

[73] Assignee: The Upjohn Company, Kalamazoo, Mich.

[22] Filed: Feb. 21, 1975

[21] Appl. No.: 551,826

Related U.S. Application Data

[60] Division of Ser. No. 381,155, July 20, 1973, abandoned, which is a continuation-in-part of Ser. No. 248,013, April 27, 1972, abandoned.

[52] U.S. Cl. .................... 260/240 R; 260/343.3 R
[51] Int. Cl.² ...................................... G07D 307/93
[58] Field of Search ...... 260/343.3, 240 R, 343.3 P

[56] References Cited

UNITED STATES PATENTS 3,864,387  2/1975  Nelson ........................... 260/473 A

OTHER PUBLICATIONS

McOmie, *Protective Groups in Organic Chemistry* pp. 95–105 (1973).

*Primary Examiner*—Robert Gerstl
*Attorney, Agent, or Firm*—Morris L. Nielsen; Robert A. Armitage

[57] ABSTRACT

Prostaglandin-type compounds with one or two fluoro substituents at the C-16 position are disclosed, with processes for making them. These compounds are useful for a variety of pharmacological purposes, including anti-ulcer, inhibition of platelet aggregation, increase of nasal patency, labor inducement at term, and wound healing.

15 Claims, No Drawings

BICYCLIC INTERMEDIATES FOR PREPARING 16-FLUORINATED PROSTAGLANDIN ANALOGS

The present application is a division of Ser. No. 381,155, filed July 20, 1973, now abandoned, which is a continuation-in-part of Ser. No. 248,013, filed Apr. 27, 1972, now abandoned.

The present invention relates to bicyclic lactone intermediates used in the preparation of prostaglandin analogs. The essential material constituting disclosure of the present invention is incorporated here by reference from U.S. Pat. No. 3,962,293.

I claim

1. An optically active compound of the formula

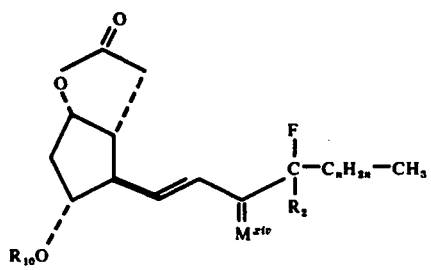

or a racemic compound of that formula and the mirror image thereof, wherein $C_nH_{2n}$ is alkylene of one to 9 carbon atoms, inclusive, with one to 6 carbon atoms, inclusive, in the chain between $-CFR_2-$ in the terminal methyl;

wherein $M^{XIV}$ is

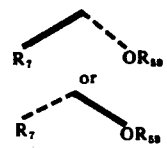

wherein $R_7$ is hydrogen or alkyl of one to 4 carbon atoms, inclusive, and $R_{59}$ is alkyl of one to 4 carbon atoms, inclusive, or on acetal or ketal blocking group;

wherein $R_2$ is hydrogen, methyl, ethyl, or fluoro;
wherein $R_{10}$ is an acetal or ketal blocking group; and
wherein an acetal or ketal blocking group is any acetal or ketal group which initially replaces the hydrogen of an hydroxyl group; which thereafter is not attacked by, nor as reactive as the hydrogen of the hydroxy to the reagents used in the preparation of prostaglandin-type products; and which ultimately is replaceable by hydrogen in the preparation of prostaglandin-type products.

2. A compound according to claim 1, wherein $M^{XIV}$ is

3. A compound according to claim 2, wherein $R_7$ is hydrogen.

4. A compound according to claim 3, wherein $R_{59}$ is an acetal or ketal blocking group.

5. A compound according to claim 4, wherein $C_nH_{2n}$ has 3 carbon atoms in the chain between $-CFR_2-$ and a terminal methyl.

6. A compound according to claim 5, wherein $R_2$ is hydrogen.

7. 3α,5α-Dihydroxy-2β-[3α-hydroxy-(4S)- and (4R)-4-fluoro-trans-1-octenyl]-1α-cyclopentaneacetic acid γ lactone, 3,3′-bis-(tetrahydropyranyl ether), compounds according to claim 6 wherein the acetal or ketal blocking group is tetrahydropyranyl.

8. A compound according to claim 7, wherein $R_2$ is fluoro.

9. 3α,5α-Dihydroxy-2β-(3α-hydroxy-4,4-difluoro-trans-1-octenyl)-1α-cyclopentaneacetic acid γ lactone, 3,3′-bis-(tetrahydropyranyl ether), a compound according to claim 8, wherein the acetal or ketal blocking group is tetrahydropyranyl.

10. An optically active compound of the formula

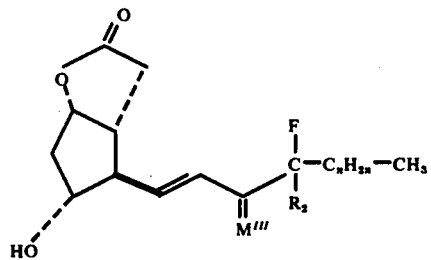

or a racemic compound of that formula and the mirror image thereof, wherein $C_nH_{2n}$ is alkylene of one to 9 carbon atoms, inclusive, with one to 6 carbon atoms, inclusive, in the chain between $-CFR_2-$ and the terminal methyl;

wherein $M^{III}$ is

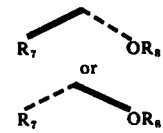

wherein $R_7$ and $R_8$ are hydrogen or alkyl of one to 4 carbon atoms, inclusive, being the same or different; and wherein $R_2$ is hydrogen, methyl, ethyl, or fluoro.

11. A compound according to claim 10, wherein $C_nH_{2n}$ has 3 carbon atoms in the chain between $-CFR_2-$ and the terminal methyl.

12. A compound according to claim 11, wherein $R_2$ is hydrogen.

13. 3α,5α-Dihydroxy-2γ-[3α-hydroxy-(4S)- and (4R)-4-fluoro-trans-1-octenyl]-1α-cyclopentaneacetic acid γ lactone, compounds according to claim 12.

14. A compound according to claim 11, wherein $R_2$ is fluoro.

15. 3α,5α-Dihydroxy-2β-(3α-hydroxy-4,4-difluoro-trans-1-octenyl)-1α-cyclopentaneacetic acid γ lactone, a compound according to claim 14.

* * * * *

UNITED STATES PATENT OFFICE
CERTIFICATE OF CORRECTION

Patent No. 4,031,081  Dated June 21, 1977

Inventor(s) Barney J. Magerlein

It is certified that error appears in the above-identified patent and that said Letters Patent are hereby corrected as shown below:

Column 2, line 13, claim 8, "7" should read --5--; line 56, "$2\gamma$" should read --$2\beta$--.

Signed and Sealed this

Fourteenth Day of February 1978

[SEAL]

Attest:

RUTH C. MASON  
Attesting Officer

LUTRELLE F. PARKER  
Acting Commissioner of Patents and Trademarks